US009448169B2

(12) United States Patent
Yoshioka et al.

(10) Patent No.: US 9,448,169 B2
(45) Date of Patent: Sep. 20, 2016

(54) LIGHT MEASURING APPARATUS, LIGHT MEASURING METHOD, FILTER MEMBER, AND METHOD OF MAKING FILTER MEMBER

(71) Applicants: KYUSHU UNIVERSITY, NATIONAL UNIVERSITY CORPORATION, Fukuoka (JP); USHIO DENKI KABUSHIKI KAISHA, Tokyo (JP)

(72) Inventors: Hiroaki Yoshioka, Fukuoka (JP); Yuji Oki, Fukuoka (JP); Kinichi Morita, Tokyo (JP)

(73) Assignees: Kyushu University, National University Corporation, Fukuoka (JP); Ushio Denki Kabushiki Kaisha, Tokyo (JP)

( * ) Notice: Subject to any disclaimer, the term of this patent is extended or adjusted under 35 U.S.C. 154(b) by 26 days.

(21) Appl. No.: 14/486,310

(22) Filed: Sep. 15, 2014

(65) Prior Publication Data

US 2015/0085282 A1    Mar. 26, 2015

(30) Foreign Application Priority Data

Sep. 20, 2013 (JP) ................................ 2013-196082
Mar. 26, 2014 (JP) ................................ 2014-064415

(51) Int. Cl.
*B41M 5/00* (2006.01)
*B41M 5/52* (2006.01)
*G02B 5/22* (2006.01)
*G02B 5/23* (2006.01)
*G01N 21/64* (2006.01)
*B41M 5/50* (2006.01)

(52) U.S. Cl.
CPC .......... *G01N 21/6402* (2013.01); *B41M 5/502* (2013.01); *B41M 5/529* (2013.01); *G02B 5/223* (2013.01); *G02B 5/23* (2013.01); *B41M 2205/02* (2013.01); *G01N 2201/068* (2013.01); *G01N 2201/06113* (2013.01); *Y10T 29/49993* (2015.01)

(58) Field of Classification Search
CPC .......... G02B 5/22; G02B 5/223; G02B 5/23; Y10T 29/499993; B41M 5/502; B41M 5/529; B41M 2205/02
USPC .......................................... 503/227; 359/885
See application file for complete search history.

(56) References Cited

U.S. PATENT DOCUMENTS 5,378,675 A * 1/1995 Takeyama ................ B41M 5/44
428/206
2008/0277606 A1 11/2008 Wang et al.

FOREIGN PATENT DOCUMENTS

JP    2009-516162 A    4/2009
JP    2014-032064 A    2/2014
WO    2012/133920 A1    10/2012

*Primary Examiner* — Bruce H Hess
(74) *Attorney, Agent, or Firm* — Studebaker & Brackett PC

(57) ABSTRACT

A light measuring arrangement maintains the initial filtering function of an optical filter having a dye dispersed therein. The light measuring arrangement includes a measuring unit configured to measure an intensity of light emitted from a measurement target at a predetermined wavelength. The light measuring arrangement also includes the optical filter unit having the dye. The light measuring arrangement also includes a dye diffusion restricting unit configured to restrict diffusion of the dye from the optical filter unit. The optical filter unit constitutes part of an optical path for the light traveling from the measurement target to the light measuring unit.

6 Claims, 17 Drawing Sheets

US 9,448,169 B2

LIGHT MEASURING APPARATUS, LIGHT MEASURING METHOD, FILTER MEMBER, AND METHOD OF MAKING FILTER MEMBER

FIELD OF THE INVENTION

The present invention relates to a light measuring apparatus, a light measuring method, a filter member, and a method of making the filter member. In particular, the present invention relates to a light measuring apparatus that includes a measuring unit for measuring an intensity of light emitted from an object (measurement target) in a certain wavelength range.

DESCRIPTION OF THE RELATED ART

In the field of optoelectronics, organic light functional materials are used in various applications. For example, an optical material which includes a macromolecular substance or polymer such as resin and an organic light functional material dispersed in the macromolecular substance (polymer) is used in a laser medium, an optical filter, an optical device and the like.

In Patent Literature 1 (PCT International Publication No. WO 2012/133920), polydimethylsiloxane (referred to as "PDMS" hereinafter) that contains, for example, a pyromethene-based dye (pigment) is proposed as a solid dye laser medium. The polysiloxane resin, such as PDMS, itself possesses a resistance to photodegradation (photo-deterioration) and good light permeability (light transmission) in a wide range of wavelength. Because the polysiloxane resin is not optically active, the polysiloxane resin is useful as a medium for dispersing the organic optical functional material.

In Patent Literature 2 (Japanese Patent Application Laid-Open Publication No. 2009-516162), a microchip has a microchannel (flow channel) to receive and discharge a sample (specimen), and is equipped with an excitation light source and a detector to prepare a micro fluid device. The micro fluid device has an optical filtering zone that selectively allows a necessary wavelength only to pass therethrough. This optical filtering zone is prepared by the PDMS having a dye dispersed therein. The dye belongs to, for examples, the Sudan dye family.

The inventors of this patent application previously proposed a light induced fluorescence measuring apparatus that can cope with a demand from a point of care testing (POCT) in the field of life science. This measuring apparatus can be used at a site where analysis is needed. The testing time of the measuring apparatus is short, and a high precision evaluation and analysis is performed. The measuring apparatus can be small and portable. For example, a laser induced fluorescence (LIF) method may be used for the measuring apparatus.

The LIF method uses a resonant transition of an atom or molecule, which is the measurement target, and irradiates the measurement target with laser beam that matches the excitation level (the laser beam wavelength is tuned in such manner) to excite the measurement target (atom or molecule). The induced light emission (fluorescence) is then measured. The density of the measurement target is calculated from the intensity of fluorescence, and the temperature of the measurement target is calculated from the spectral distribution of fluorescence.

FIG. 7 of the accompanying drawings shows an exemplary configuration of a light induced fluorescence measuring apparatus 101 that is proposed by the inventors. The light induced fluorescence measuring apparatus 101 is disclosed in Patent Literature 3 (Japanese Patent Application Laid-Open Publication No. 2014-32064). The light induced fluorescence measuring apparatus 101 includes a solid light source 103 such as a laser light source, a sample casing 105 for holding a measurement sample, a fluorescence collecting (fluorescence convergent) optical system 107 including lenses, optical filters and other components, and a fluorescence measuring unit 109 such as a photomultiplier tube. It should be noted that Patent Literature 3 was published after the priority date of the subject application. The publication date of Patent Literature 3 is Feb. 20, 2014, and the priority date of the subject application is Sep. 20, 2013.

The sample casing 105 is transparent to the light including the excitation light emitted from the solid light source 103 and the fluorescence emitted from the sample. The sample casing 105 is installed in the laser beam irradiation space 110. The solid light source 103, the sample casing 105, the fluorescence collecting optical system 107 which includes the lenses and optical filters, and the fluorescence measuring unit 109 are buried (embedded) in the resin 111 (e.g., PDMS) that is transparent to the light including the excitation light and the fluorescence. At least part of the optical path that guides the fluorescence of the fluorescence collecting optical system 107 is filled with the transparent resin 113 such as PDMS.

More specifically, the sample casing 105 is transparent to the light including the excitation light emitted from the solid light source 103 and the fluorescence emitted from the sample. The solid light source 103, the sample casing 105, the fluorescence collecting optical system 107 including the lenses and optical filters, and the fluorescence measuring unit 109 are buried in the resin 11 such as PDMS that is transparent to the light including the excitation light and the fluorescence. At least part of the optical path that guides the fluorescence of the fluorescence collecting optical system 107 is also filled with the transparent resin 113 such as PDMS. Thus, the transparent resin integrally holds the sample casing 105, the fluorescence collecting optical system 107 and the fluorescence measuring unit 109.

The transparent resin structure that integrally holds the respective components is enclosed (encapsulated) by the resin 111 that uniformly contains a pigment having a wavelength characteristic to absorb the excitation light, the intrinsic fluorescence (autofluorescence) generated when the sample casing is irradiated with the excitation light, and the Raman light generated from the resin when the excitation light proceeds in the resin.

A power source 114 to feed electricity to the solid light source 103 and the fluorescence measuring unit 109 when necessary is embedded in the resin 111 which contains the pigment. In other words, the pigment-containing resin 111 defines a housing or frame (chassis) to hold the sample casing 105, the fluorescence measuring unit 109 and the fluorescence collecting optical system 107.

As such, because the respective structural parts of the light induced fluorescence measuring apparatus 101 are buried in the resin 111 in the above-described manner, the positions of the optical elements and other components do not change easily even if vibrations and shocks are applied on the light induced fluorescence measuring apparatus 101. As a result, the disalignment (misalignment) of the fluorescence collecting optical system 107 is restricted or prevented. In addition, the adhesion between the resin 111 and the optical elements is good, and undesired reflection and scattering of the light hardly take place, which would otherwise be generated by the air present at the interface (contacting portion) between the resin and the optical elements.

Thus, this configuration is stable against the external shock, and does not need holders to hold the optical elements. Accordingly, the light induce fluorescence measuring apparatus 101 can be compact and portable.

Also, because the resin 111 that is configured to enclose the housing substantially uniformly contains a pigment having a wavelength characteristic to absorb the excitation light, the intrinsic fluorescence generated when the sample casing is irradiated with the excitation light, and the Raman light generated from the resin when the excitation light proceeds in the resin, the excitation light and the fluorescence, which is the measuring beam, are not emitted to the outside from the measuring apparatus 101, and the external light does not enter the fluorescence collecting optical system 107 and other components. Therefore, highly precise measurement is possible.

When the material of the pigment-containing resin 111 is the same as the material of the transparent resin 113 in which the solid light source 103, the sample casing 105, the fluorescence collecting optical system 107 and other components are buried, these two resins 111 and 113 have the same refractive index and therefore no refractive index boundary appears on the interface between the two resins. Thus, the reflection and scattering of the light at the interface between the two resins is suppressed. Once the excitation light and its stray light such as the reflection light and scattered light are incident to the pigment-containing resin 111, the excitation light and the stray light are absorbed, and complicated multiple reflection of the stray light hardly occurs. Thus, the fluorescence collecting optical system does not have to cope with the complicated multiple reflection of the stray light, and can have a simple structure. As a result, the light induced fluorescence measuring apparatus 101 can be downsized.

LISTING OF REFERENCES

Patent Literatures

PATENT LITERATURE 1: PCT International Publication No. WO 2012/133920
PATENT LITERATURE 2: PCT Application Japan's National Publication No. 2009-516262 (WO 2007/061478)
PATENT LITERATURE 3: Japanese Patent Application Laid-Open Publication No. 2014-32064-A (Japanese Patent Application No. 2012-171825)

SUMMARY OF THE INVENTION

Problem to be Solved

In the light induced measuring apparatus (LIF measuring apparatus) 101, the fluorescence collecting optical system 107 includes a plurality of condenser lenses (collecting lenses) 115 and 117, and a plurality of optical filters 119, 121, 123, 125 and 127. The optical filters 119, 121, 123, 125 and 127 may include, for example, notch filters that reflect the light having the wavelength equal to the wavelength of the excitation light emitted from the solid light source, and color glass filters that absorb the light other than the fluorescence emitted from the sample.

When the optical filter is prepared from the silicone resin such as PDMS and the dye contained in the silicone resin, and the dye absorbs the light other than the fluorescence emitted from the sample, such optical filter becomes an organic light functional material having a similar optical characteristic to the color glass filter. Preparation (molding) of the silicone resin is relatively easy, and the shape of the silicon resin has a high degree of freedom. Thus, it is possible to easily obtain the organic light functional material that has a shape corresponding to the optical path of the fluorescence collecting optical system 107.

On the other hand, however, when such optical filter is used in the light induced measuring apparatus 101, the following shortcomings arise.

As described in Patent Literature 1, when PDMS is used as the silicone resin that is a solid medium to which the dye is added and dispersed therein, the dye in PDMS moves inside a nano-porous structure because PDMS has the nano-porous structure. When the optical filter made from the dye-containing resin such as PDMS is placed in the atmosphere, the dye does not pass through the interface between the optical filter surface and the atmosphere, and is not released to the atmosphere. The dye moves only inside the optical filter, which is the solid medium.

However, if such optical filter is buried in the resin 111 such as PDMS, as in the light induced measuring apparatus 101, the outer surface of the optical filter tightly (firmly) contacts the resin 111 such as PDMS. When the resin 111 to bury (embed, receive or enclose) the optical filter therein is PDMS, the resin naturally has the nano-porous structure. In a certain case, therefore, the dye dispersed in the optical filter may pass through the interface between the optical filter and the PDMS resin, in which the optical filter is buried, and leak into the resin 111 from the optical filter.

The PDMS resin in which the optical filter is buried has a larger volume than the optical filter (i.e., the solid medium). Thus, once the dye moves into the PDMS resin in which the optical filter is buried, the probability of re-invasion of the dye into the optical filter from the PDMS resin decreases. Accordingly, the dye dispersed in the optical filter gradually moves to the outside, and the optical filter becomes difficult to perform the desired (expected) performances.

In the light induced measuring apparatus 101, the resin 111 for enclosing the housing in which the optical path for the fluorescence extends does not contains a dye but the pigment as the material to absorb the excitation light, the intrinsic fluorescence generated when the sample casing is irradiated with the excitation light, and other light. This is because the pigment does not move in the resin 111 regardless of the type of the resin, and exists stably. Thus, the pigment does not move (leak) through the interface between the resin that constitutes the housing including the optical path for the fluorescent and the resin that contains the pigment, and the interface (boundary) between the two resins does not become not obscure.

However, when the pigment is contained in the resin such as PDMS, the pigment has a large grain diameter and the incident light is scattered. Thus, it is difficult to configure the optical filter that has a similar optical characteristic to the color glass filter if the pigment is contained in the resin such as PDMS. Consequently, it is difficult to use the structure that is made from the pigment-containing resin, as the optical filter, in the light induced measuring apparatus 101 having the above-described configuration.

The present invention is developed in view of these facts, and an object of the present invention is to provide a light measuring apparatus and method that can maintain the initial filtering function of the optical filter having a dye dispersed therein, and to provide a filtering member used in such light measuring apparatus, and a method of making the filtering member.

Solution to the Problem

According to a first aspect of the present invention, there is provided a light measuring apparatus that includes a measuring unit configured to measure an intensity of light emitted from a measurement target at (or in) a predetermined wavelength. The light measuring apparatus also includes a first optical filter unit having a first dye, and a dye diffusion restricting unit configured to restrict diffusion of the first dye from the first optical filter unit. The first optical filter unit constitutes part of an optical path for the light traveling from the measurement target to the light measuring unit.

According to a second aspect of the present invention, the light measuring apparatus of the first aspect may further include a light absorbing unit placed between the first optical filter unit and the dye diffusion restricting unit and configured to absorb light having a wavelength other than the wavelength of the light emitted from the measurement target.

According to a third aspect of the present invention, the light absorbing unit of the light measuring apparatus of the second aspect may be made from the same material as the first optical filter unit, and may contain a second dye which is different from the first dye.

According to a fourth aspect of the present invention, the light measuring apparatus of any one of the first to third aspects may further include a second optical filter unit provided on the optical path and configured to absorb or reflect light having a wavelength other than the wavelength of the light emitted from the measurement target. The first optical filter unit may constitute part of the optical path between the second optical filter unit and the measuring unit.

According to a fifth aspect of the present invention, the light measuring apparatus of the fourth aspect may further include a first lens provided on the optical path and configured to convert the light emitted from the measurement target to parallel light, and a second lens provided on the optical path and configured to condense the parallel light. When the light having the predetermined wavelength is incident on the second optical filter unit at the incident angle of 0 degree, the second optical filter unit may shield (block off) the light most efficiently. The first lens may be located on the optical path between the measurement target and the second optical filter unit, and the second lens may be located on the optical path between the second optical filter unit and the measuring unit.

According to a sixth aspect of the present invention, the light measuring apparatus of the fifth aspect may further include a housing (frame) configured to house the optical path, the first lens, the second optical filter unit, the second lens, the first optical filter unit, and the dye diffusion restricting unit. Each of the first lens and the second lens may include an air layer (air space). The optical path, the first optical filter unit and the housing may be made from resin.

According to a seventh aspect of the present invention, the optical path, the first optical filter unit and the housing of the light measuring apparatus of the sixth aspect may be made from the same resin. The dye diffusion restricting unit may be provided between the first optical filter unit and the housing.

According to an eighth aspect of the present invention, there is provided a light measuring method of measuring an intensity of light emitted from a measurement target. The light measuring method measures the light that passes through an optical filter unit equipped with a dye diffusion restricting unit configured to restrict diffusion of a dye to the outside.

According to a ninth aspect of the present invention, there is provided a filter member that has a dye dispersed unit. A dye is dispersed in the dye dispersed unit. The dye dispersed unit is configured to allow, at least, light having a predetermined (particular) wavelength to pass therethrough. The filter member also includes a dye diffusion restricting member provided adjacent to the dye diffused unit and configured to restrict diffusion of the dye from the dye diffused unit.

According to a tenth aspect of the present invention, there is provided a method of fabricating a filter member having a dye dispersed unit. A dye is dispersed in the dye dispersed unit. The filter member fabrication method includes pouring a liquid resin into a container that contains a dye diffusion restricting member. The dye diffusion restricting member is configured to restrict diffusion of the dye from the dye dispersed unit. The filter member fabrication method also includes solidifying the liquid resin. The filter member fabrication method also includes immersing the container which contains the solidified resin, into a dye solution which contains the dye, thereby causing the dye to diffuse in the solidified resin and providing the dye dispersed unit.

According to an eleventh aspect of the present invention, there is provided another method of fabricating a filter member having a dye dispersed unit. A dye is dispersed in the dye dispersed unit. The filter member fabrication method includes dispersing the dye in a liquid resin, and pouring the liquid resin, in which the dye is dispersed, into a container that contains a dye diffusion restricting member. The dye diffusion restricting member is configured to restrict diffusion of the dye from the dye dispersed unit. The filter member fabrication method also includes solidifying the liquid resin, in which the dye is dispersed, to provide the dye dispersed unit.

In each of the above-described aspects of the present invention, the dye diffusion restricting unit restricts (reduces, prevents) the diffusion of the dye to the outside from the (first) optical filter unit. Therefore, it is possible to provide a light measuring apparatus and light measuring method as well as a filter member and its fabrication method, that can maintain an initial filtering function of the (first) optical filter unit.

As described above, it is desired that the reflection and scattering of the light is restricted. In view of this, it is not preferred to provide a dye diffusion restricting unit that is made from a different material. Each of the above-described aspects of the present invention is developed on a recognition that the diffusion of the dye to the housing from the first optical filter unit having the dye may be disadvantageous, and is characterized by provision of the dye diffusion restricting unit.

The second aspect of the present invention may ensure the optical path for the light from the measurement target while restricting the reflection and scattering at the first optical filter unit.

In the third aspect of the present invention, the light absorbing unit and the first optical filter unit may be made from the same material. Thus, the light absorbing unit and the first optical filter unit may have the same refractive index. Therefore, the restriction of the reflection and scattering at the interface between the light absorbing unit and the first optical filter unit may be more facilitated.

In the fourth aspect of the present invention, only the light which has passed the second filter unit may reach the first optical filter unit. Thus, generation of the fluorescence due to the dye contained in the first optical filter may be restricted to the minimum, and reduction of measurement noises may be facilitated.

In the fourth aspect of the present invention, the measuring unit may easily measure the light having a desired wavelength (wavelength to be measured) with no large load being exerted (e.g., the dye of the first optical filter unit is not irradiated with high-intensity excitation light).

In the fifth aspect of the present invention, the optical path may easily enable the second filter unit to function more effectively.

In the sixth aspect of the present invention, the resin may be a dominant material of the light measuring apparatus. Thus, the light measuring apparatus may be molded easier and may easily have a reduced weight.

In the seventh aspect of the present invention, the first optical filter unit may easily restrict the reflection and scattering of the light to the optical path from the housing, and generation of stray light while maintaining the initial filtering function.

In the tenth and eleventh aspects of the present invention, it may be possible to easily fabricate the filter member that includes the dye dispersed unit which has the filtering function and the dye diffusion restricting unit which has the dye diffusion preventing function.

These and other objects, aspects and advantages of the present invention will become apparent to a skilled person from the following detailed description when read and understood in conjunction with the appended claims and drawings.

DETAILED DESCRIPTION OF THE INVENTION

Now, embodiments of the present invention will be described with reference to the accompanying drawings. It should be noted that the present invention is not limited to the illustrated and described embodiments, and the embodiments of the present invention are not limited to the illustrated and described embodiments.

First Embodiment

Figure 1:
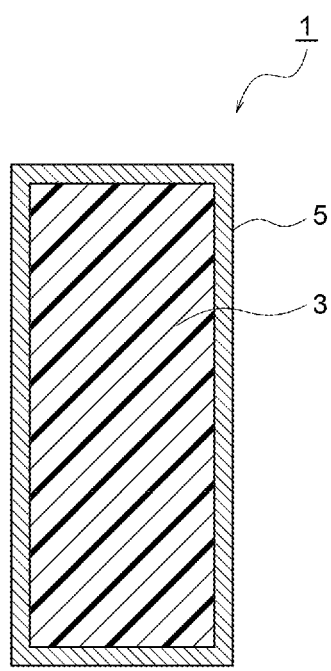
FIG. 1 is a cross-sectional view of a structure 1 according to one embodiment of the present invention.

FIG. 1 illustrates a cross-sectional view of a structure 1 (an example of "filter member" in the claims) that includes a silicone resin 3, which contains a dye, (an example of "dye dispersed unit" in the claims) according to an embodiment of the present invention. As shown in FIG. 1, the structure 1 of this embodiment has a dye diffusion restricting member 5 (an example of "dye diffusion restricting unit" and "dye diffusion restricting member" in the claims) on at least part of the surface of a formed body (molded body). In the formed body, the dye (example of "dye" in the claims) is added to a silicone resin such as PDMS, and the dye is contained in the silicone resin. FIG. 1 shows an example when the entire surface of the formed body is covered with the dye diffusion restricting member 5.

The dye diffusion restricting member 5 is made from a material that has a high density, is highly permeable to the predetermined (desired) light, and only allows negligible movements of the dye (or does not allow any movement of the dye) in the dye diffusion restricting member 5.

Specifically, an acryl resin such as poly methyl methacrylate (PPMA) resin, polyethylene terephthalate (PET), polycarbonate, inorganic glass or the like is used as the material of the dye diffusion restricting member 5. In particular, if the movements of the dye should be completely prevented, it is preferred that inorganic glass is used as the material of the dye diffusion restricting member 5.

It should be noted that a metal may be used as the material of the dye diffusion restricting member 5. When the structure 1 is used as a filter member, however, the light incident on the surface of the dye diffusion restricting member 5 that contacts the surface of the dye-containing formed body is reflected and scattered by the surface of the dye diffusion restricting member 5, and the light may proceed (travel) to an undesired direction. Thus, it is not preferred to employ the metal as the material of the dye diffusion restricting member 5 when the structure 1 is used as the filter member.

When the structure 1 is buried in the formed body made from the silicon resin such as PDMS, the dye diffusion restricting member 5 is provided on at least that area of the structure 1 which contacts the buried silicon resin. Then, the dye contained in the structure 1 hardly enters the dye diffusion restricting member 5 although the dye moves inside the structure 1. Because the interface between the structure 1 and the silicon resin-made formed body in which the structure 1 is buried is the interface between the dye diffusion restricting member 5 and the silicon resin, the dye contained in the structure 1 does not leak from the interface to the silicon resin-made formed body which is outside the structure 1.

Therefore, when the structure 1 is used as the optical filter, the dye dispersed in the optical filter does not gradually move to the outside, and the prescribed (initial) functions of the optical filter are maintained.

When the structure 1 contains a dye that absorbs predetermined light and serves as an optical filter, such optical filter becomes an organic light functional member that has a similar characteristic (performance) to a color glass filter. As described above, the preparation (forming, molding) of the silicon resin 3 is relatively easy, and the shape of the silicon resin 3 has a high degree of freedom. Thus, it is possible to easily obtain the organic light functional member that has a shape corresponding to the shape of the optical path of the optical system.

First Method of Making the Structure 1

An exemplary method of making the structure 1 will now be described. In the following example, the structure 1 is used to configure the optical filter.

Figure 2A:
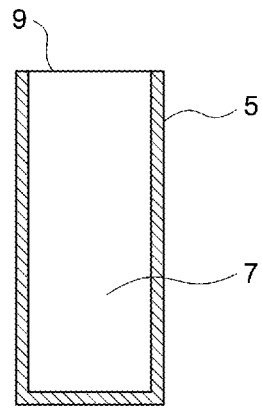
FIG. 2A to FIG. 2G is a series of views useful to describe an exemplary method of fabricating a structure that is made from a dye-containing silicon according to the embodiment of the present invention.

At first, as shown in FIG. 2A, a dye diffusion restricting member 5 is fabricated. The dye diffusion restricting member 5 is made from, for example, inorganic glass. The outer shape of the dye diffusion restricting member 5 corresponds to, for example, the shape of the optical path, in which the dye diffusion restricting member 5 is installed. The dye diffusion restricting member 5 has a cavity (hollow portion) 7 therein, and also has an opening 9 that is spatially continuous to the cavity 7. As will be described later, a silicon resin such as PDMS that contains a dye is placed in the cavity 7.

Figure 2B:
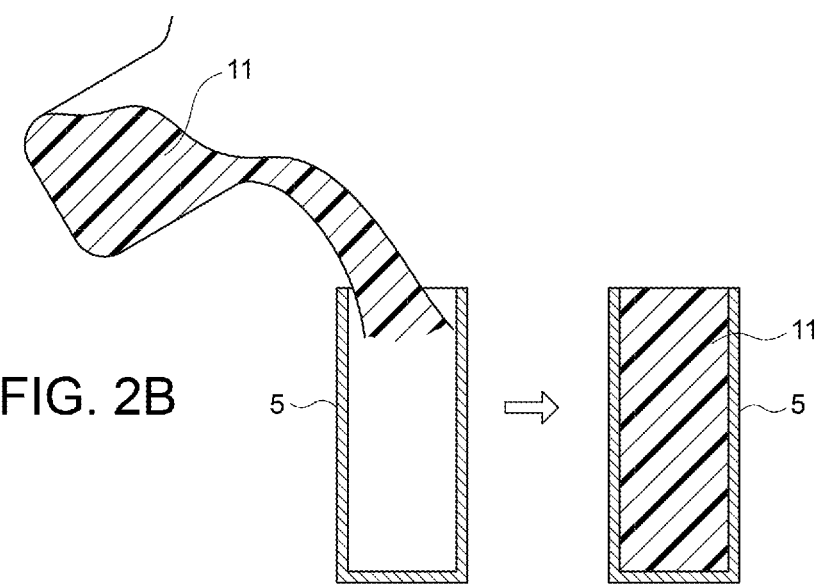

Subsequently, as shown in FIG. 2B, the liquid silicon resin 11 (example of "liquid resin" in the claims) is poured from the opening 9 of the dye diffusion restricting member 5. Then, additives such as a polymerization initiator, a curing agent (hardener), a crosslinking agent and the like are appropriately added depending upon the characteristics of the silicon resin 11 to be used, such that the cavity 7 is filled with the liquid silicon resin 11 to which the additives are added.

Figure 2C:
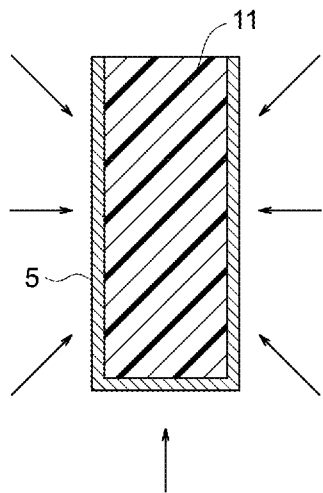

Then, as shown in FIG. 2C, the liquid silicon resin 11 poured in the cavity 7 of the dye diffusion restricting member 5 is cured. The silicon resin 11 is cured by leaving the silicon resin 11 for a certain time at the room temperature, or by heating the silicon resin 11 for a certain time, depending upon the silicon resin 11 in use. When the silicon resin 11 is a UV curable resin, the silicon resin 11 is irradiated with a curing beam to cure the silicon resin 11. FIG. 2C shows an example when the liquid silicon resin 11 is cured by heating. The black arrows in FIG. 2C represent the heating.

Figure 2D:
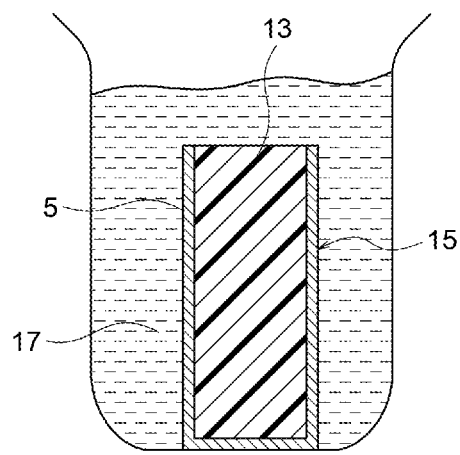

Subsequently, as shown in FIG. 2D, the silicon resin 11 is cured in the cavity 7, and the dye diffusion restricting member 5 becomes integral with the silicon resin 13 to form a structure 15. The structure 15 is immersed in a dye solution 17 (example of "dye solution" in the claims). The dye solution 17 is prepared by, for example, dissolving a dye in an organic solvent such as alcohol.

Figure 2E:
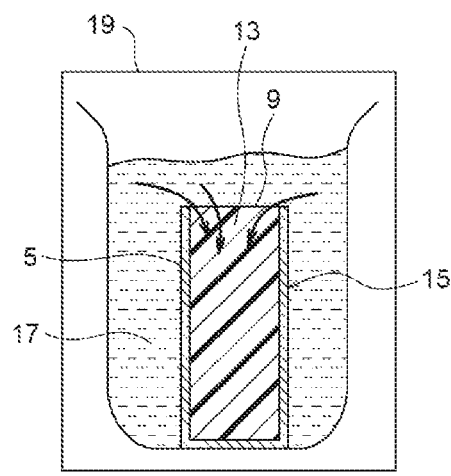

As shown in FIG. 2E, a thermostatic bath or oven 15 (heating tank) or the like is used to heat the structure 15, which is immersed in the dye solution 17, for a certain time such that the dye diffuses into the silicon resin 13 from the opening 9.

Figure 2F:
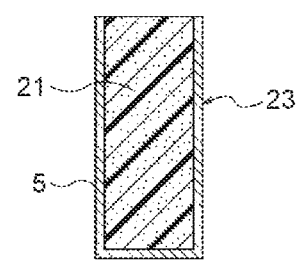

Then, as shown in FIG. 2F, the structure 23 that has the dye-containing silicon resin 21 is taken out of the thermostatic bath 19 or the like together with the dye solution 17.

After the structure 23 is taken out of the dye solution 17, the structure 23 is left for a predetermined time at the room temperature.

The structure 23 of this embodiment is prepared by the above-described steps.

Figure 2G:
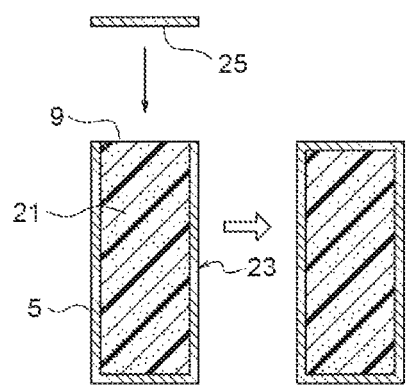

In the situation shown in FIG. 2F, the dye-containing silicon resin 21 is exposed at the opening 9 of the dye diffusion restricting member 5. If the exposed portion should also be covered with dye diffusion restricting member 5, a lid member 25 that is made from the same (or similar) material as the dye diffusion restricting member 5 is attached over the opening 9, as shown in FIG. 2G. The lid member 25 is attached by, for example, welding.

Second Method of Making the Structure 1

In the above-described method of making the structure 1, the liquid silicon resin 11 is introduced into the dye diffusion restricting member 5 and the silicon resin 11 is solidified. Then, the dye is dispersed in the solidified silicon resin 13. It should be noted, however, that the method of making the structure 1 according to the present invention is not limited to such method. For example, a liquid silicon resin, in which a dye is dispersed beforehand, may be introduced into the dye diffusion restricting member 5, and the silicon resin may be solidified. This method will be described below.

Figure 3A:
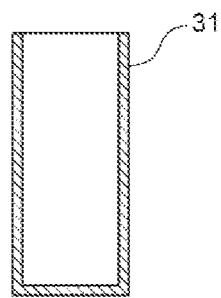
FIG. 3A to FIG. 3F is a series of views useful to describe another exemplary method of fabricating the structure that is made from a dye-containing silicon according to the present invention.

As shown in FIG. 3A, firstly, a dye diffusion restricting member 31 is prepared. The dye diffusion restricting member 31 is made from, for example, inorganic glass, and is formed to have an outer shape that corresponds to the shape of the optical path in which the dye diffusion restricting member 31 is installed. The dye diffusion restricting member 31 has a cavity (hollow portion) therein, and also has an opening that is spatially continuous to the cavity. As will be described later, a silicon resin such as PDMS that contains a dye is placed in the cavity.

Figure 3B:
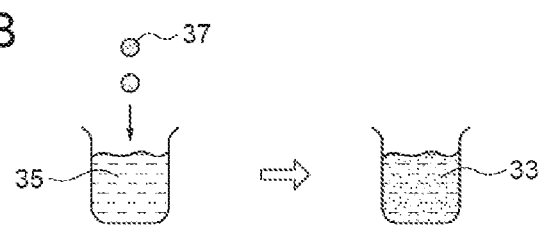

Subsequently, as shown in FIG. 3B, a dye solution 33 is prepared. The dye solution 33 is obtained by, for example, dissolving a dye 37 in a solvent 35 such as a volatile solvent (e.g., alcohol, toluene or the like), silicon oil or the like.

Figure 3C:
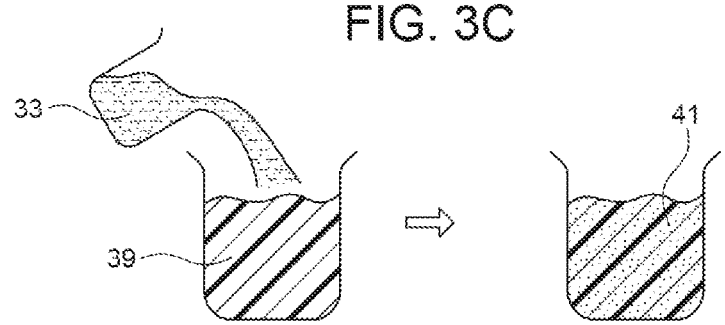

Then, as shown in FIG. 3C, a liquid silicon resin 39 and the dye solution 33, which is prepared at the step shown in FIG. 3B, are mixed with each other to prepare a liquid mixture 41 of the liquid silicon resin 39 and the dye solution 33.

An additive (or additives) such as polymerization initiator, a curing agent (hardener), a crosslinking agent and the like may be added appropriately, depending upon the characteristic of the liquid silicon resin 39 to be used.

If a volatile solvent is used when the dye solution 33 is prepared, the volatile solvent is evaporated from the prepared liquid mixture 41 to remove the volatile solvent. The liquid mixture 41 may be heated in order to facilitate the removal of the volatile solvent, but the dye may be deteriorated upon heating. Therefore, it is preferred that the evaporation takes place at the room temperature under a reduced pressure. Suitable time for the removal may be decided in view of the given conditions.

Figure 3D:
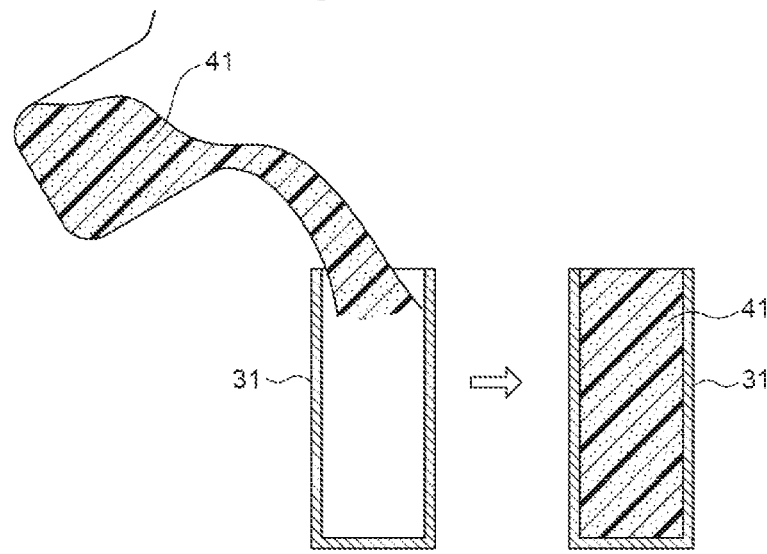

Then, as shown in FIG. 3D, the liquid mixture 41 is poured from the opening of the dye diffusion restricting member 31 such that the cavity of the dye diffusion restricting member 31 is filled with the liquid mixture 41.

Figures 3E, 3F:
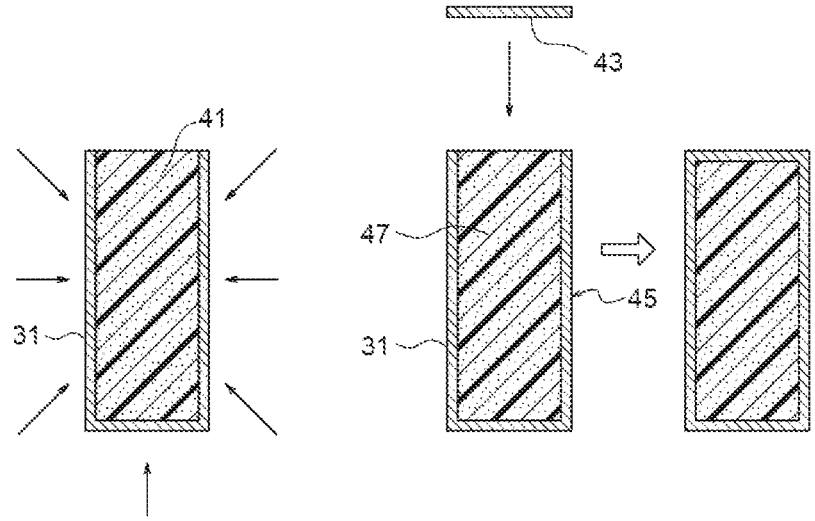

As shown in FIG. 3E, the liquid mixture 41 received in the cavity of the dye diffusion restricting member 31 is cured. The silicon resin 39 is cured by, for example, leaving the silicon resin 39 at the room temperature for a predetermined time, or heating the silicon resin 39 for a certain time, depending upon the type of the silicon resin 39. When the silicon resin 39 is a UV curable resin, the silicon resin 39 is irradiated with a curing beam to cure the silicon resin 39. FIG. 3E illustrates an example where the silicon resin 39 in the liquid mixture is heated for curing. The black arrows represents the heating.

The structure is prepared by the above-described steps of this fabrication method.

It should be noted in FIG. 3E that the dye-containing silicon resin 47 is exposed at the opening of the dye diffusion restricting member 31. If the exposed portion should also be covered with the dye diffusion restricting member 31, a lid member 43 may be placed (attached) over the opening of the dye diffusion restricting member 31, as shown in FIG. 3F. The lid member 43 may be made from the same material as (or a similar material to) the dye diffusion restricting member 31. The lid member 43 may be attached by, for example, welding.

Out of the above-described two fabrication methods, the first fabrication method solidifies the silicon resin 11 received in the cavity 7 of the dye diffusion restricting member 5 and the dye is diffused in the silicon resin 13 whereas the second fabrication method firstly mixes the liquid silicon resin 39 with the dye solution 33 to prepare the liquid mixture 41, and pours the liquid mixture 41 in the cavity of the dye diffusion restricting member 31 to solidify the liquid mixture 41. Any of these two methods can be employed to make the structure 1.

Experiments of the inventors revealed that the first fabrication method may be preferred when a certain dye is used.

A liquid PDMS was used as the liquid silicon resin. This liquid PDMS was prepared by mixing the base resin (SIM-360; Shin-Etsu Chemical Co., Ltd.) with the curing agent (CAT-360; Shin-Etsu Chemical Co., Ltd.). The liquid PDMS and a dye solution, which was obtained by dissolving Sudan I (1-phenylazo-2-naphthalenol) in toluene, were used to fabricate the structure 1 by the first fabrication method and the second fabrication method.

When the second fabrication method was employed and the liquid mixture 41 was cured and solidified by the step shown in FIG. 3E, most of the dye in the liquid mixture 41 was decolorized (bleached). Thus, the structure 1 was difficult to be used as the optical filter. Although the reason for the decolorization of the dye was not obvious, it was assumed that the curing agent (CAT-360) reacted with the dye during the crosslinking reaction upon solidification of the liquid mixture 41 and the dye was decolorized.

On the other hand, when the first fabrication method was employed, the dye diffused in the solidified PDMS was not decolorized, and other shortcomings were not encountered. The dye dispersed in the PDMS properly.

From the above-described experimental results, the inventors confirmed that the structure 1 may be preferably fabricated by the first fabrication method depending upon the type of silicon resin and the dye to be used.

The structure 1 was prepared with the dye shown in Table 1, with an intention of preparing an optical filter that could absorb light at a wavelength equal to or shorter than 600 nm (specifically, wavelength equal to or shorter than 570-580 nm). The dye solution included a dye and toluene (solvent) and had a concentration of 0.1 mg/ml. The base resin (SIM-360) was mixed with the curing agent (CAT-360) to prepare a liquid PDMS. The first fabrication method was carried out with the dye solution and the liquid PDMS to make the optical filter. PMMA was used as the dye diffusion restricting member 5.

TABLE I

| Example # | Name (Dye) | Fluorescence | Solvent |
|---|---|---|---|
| (1) | Sudan II | Slightly increased in PDMS | Toluene |
| | Sudan III | | |
| (2) | Sudan I | | Toluene |
| (3) | Solvent Orange 60 | Observed | Toluene |
| (4) | Solvent Orange 22 | | Toluene |
| (5) | Solvent Yellow 14 | Increased in PDMS | Toluene |

Figure 4:
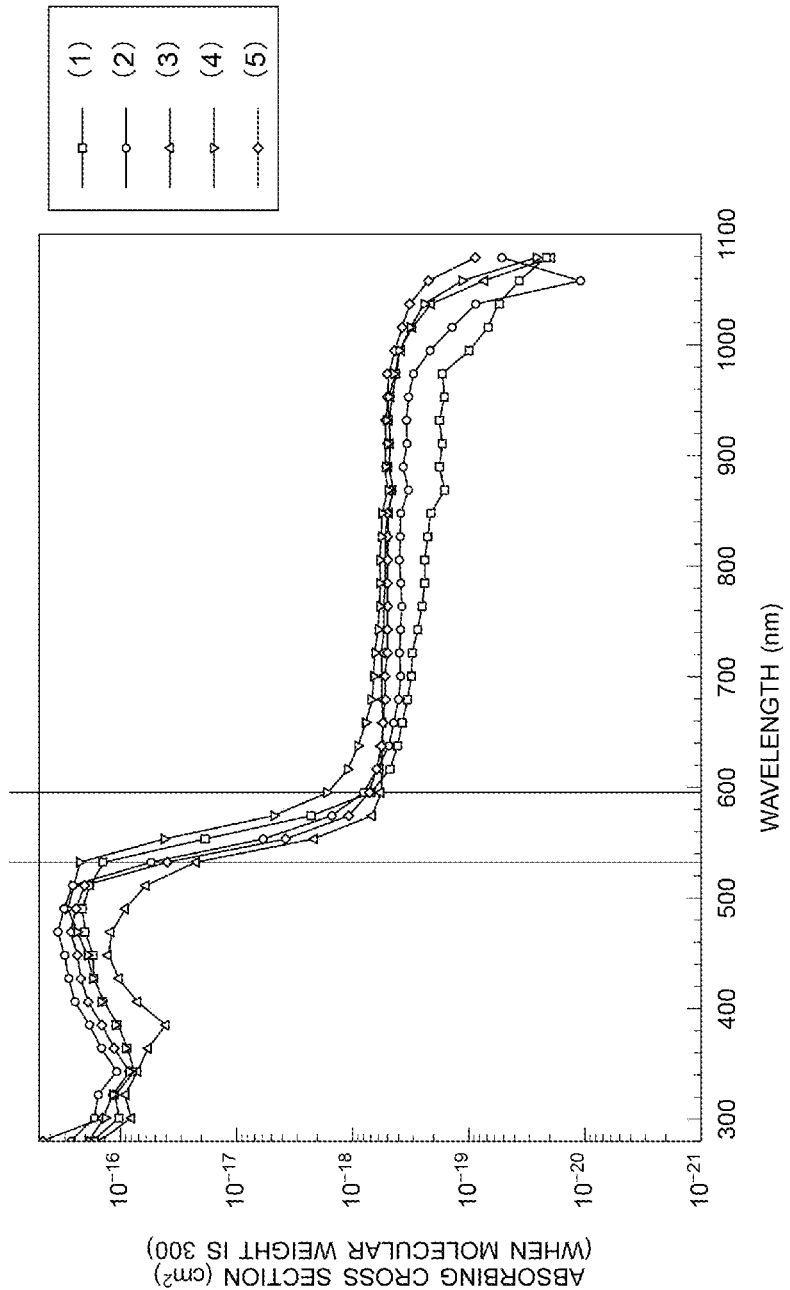
FIG. 4 shows spectral characteristics of absorbing cross sections based on calculation results.

The absorbing cross sections of the respective optical filters were calculated. FIG. 4 shows spectral characteristics of the absorbing cross sections based on the calculation results. It was confirmed from FIG. 4 that the optical filters which used the dyes of the Examples #(1), #(2) and #(5) in Table I were hopeful (preferred) when the permeability at or around the wavelength of 600 nm was considered.

Figure 5:
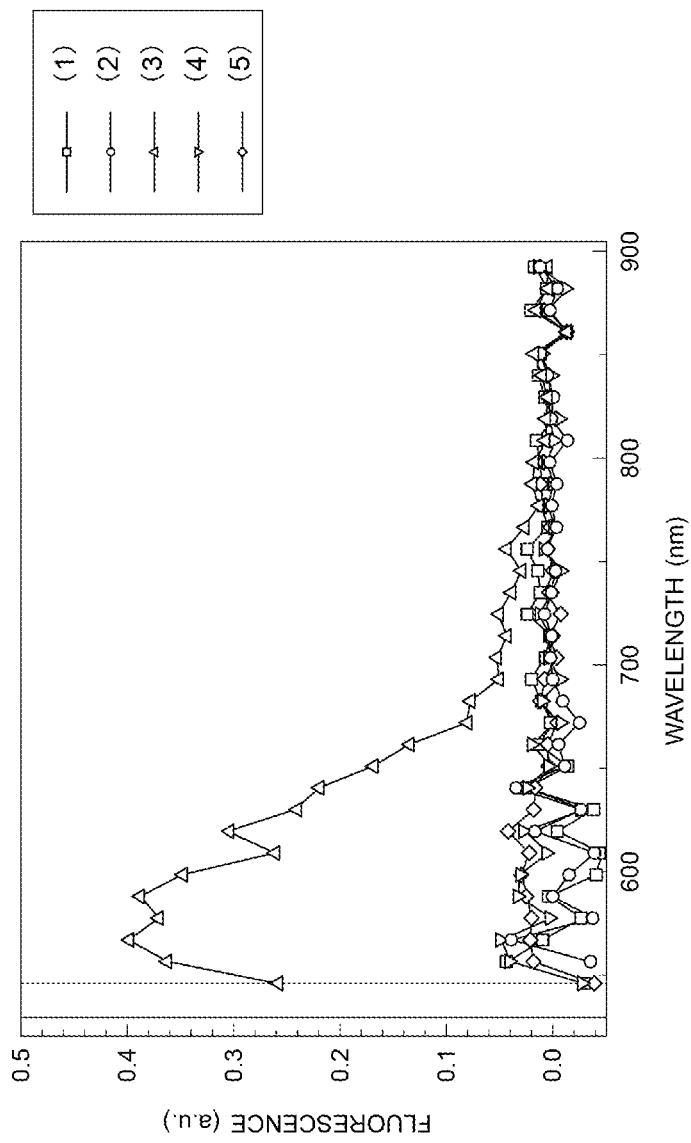
FIG. 5 shows fluorescence characteristics of optical filters prepared with various dyes.

Referring to FIG. 5, the fluorescence characteristics of the optical filters prepared with the respective dyes will be described. Except for the optical filter prepared with the dye of the Example #(3), substantially no fluorescence was observed in all the optical filers. In FIGS. 4 and 5, the same markers are used for indicating the data for the same dyes.

From the above-described results, it was confirmed that the structure 1 could be used as the optical filter when the dyes and silicon resins were appropriately selected.

Figure 6:
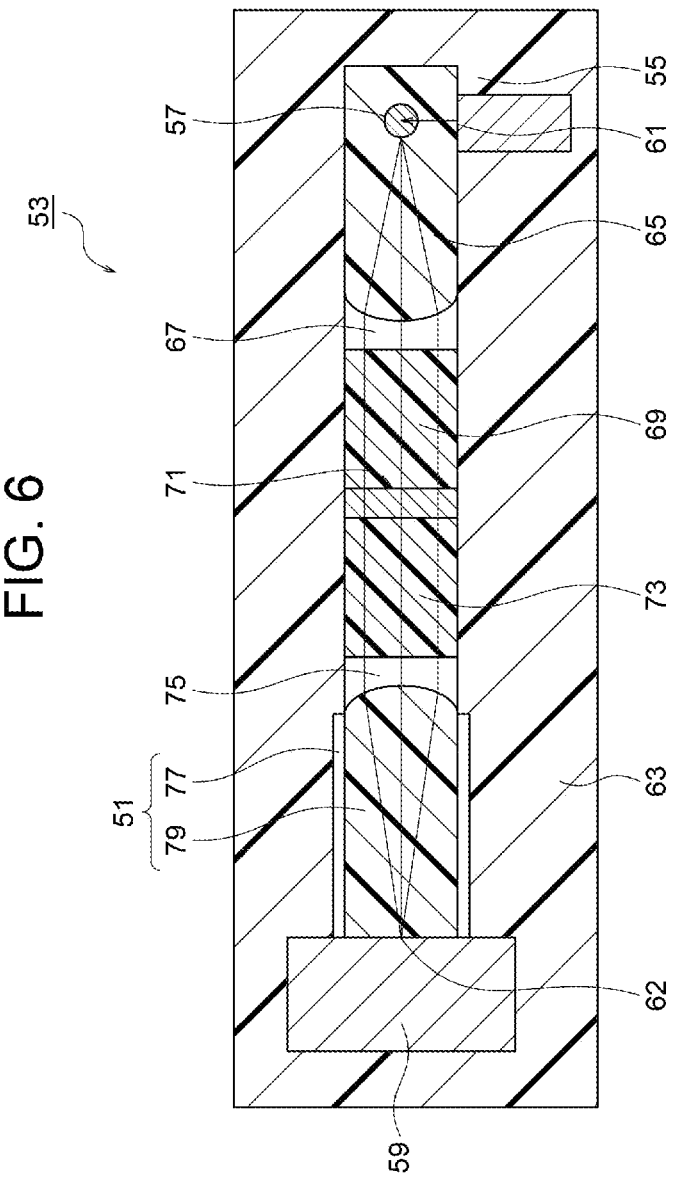
FIG. 6 illustrates an exemplary light induced fluorescence measuring apparatus (LIF measuring apparatus) that has, as an optical filter, a structure made from a dye-containing silicon resin according to the embodiment of the present invention.

Application Example of the Optical Filter According to the Embodiment of the Present Invention The following description will describe an example where the structure 1 is configured as the optical filter 51 (example of "first optical filter unit" or "optical filter" in the claims), and the optical filter 51 is used in a light induced fluorescence measuring apparatus 53 (LIF measuring apparatus) shown in FIG. 6.

Figure 7:
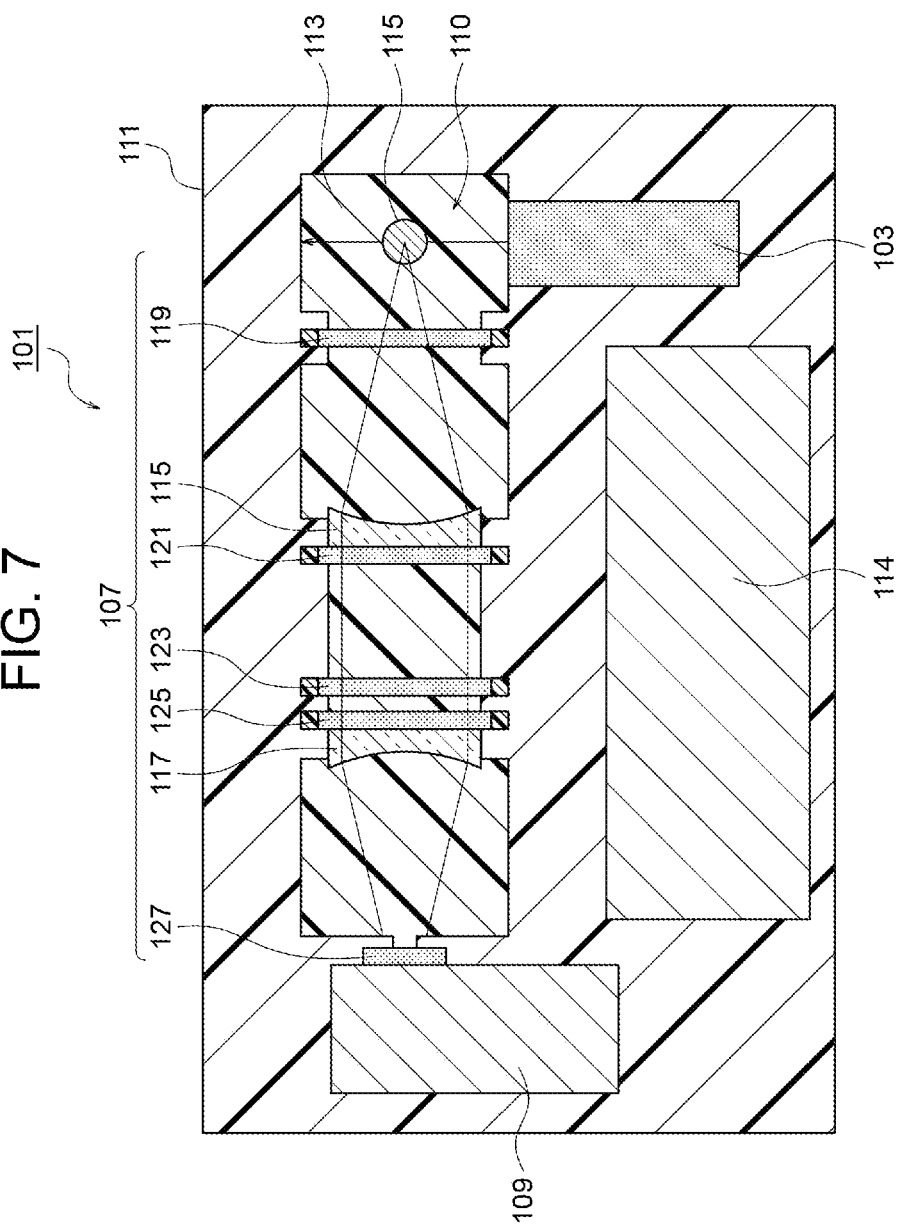
FIG. 7 illustrates an example of a light induced fluorescence measuring apparatus proposed by the inventors.

The light induced fluorescence measuring apparatus 53 shown in FIG. 6 is similar to the apparatus shown in FIG. 7, and includes a solid light source 55 such as a laser light source, a sample casing 57 configured to hold measurement samples, a fluorescence collecting optical system having lenses, optical filters and other components, and a fluorescence measuring unit 59 such as a photo multiplier tube (example of "measuring unit" in the claims).

Specifically, at least the light emitting surface 61 of the laser light source (solid light source 55) and the light receiving surface 62 of the photo multiplier tube (fluorescence measuring unit 59) are buried in (or in contact with) the transparent resin such as PDMS that is transparent to the light including the excitation light from the solid light source 55 and the fluorescence emitted from the sample. The fluorescence collecting optical system formed on the optical path from the light emitting surface 61 to the light receiving surface 62 is also buried in the transparent resin such as PDMS, or the transparent resin itself constitutes the fluorescence collecting optical system. In other words, the light emitting surface 61 of the laser light source, the sample casing 57, the fluorescence collecting optical system (example of "optical path" in the claims), and the light receiving surface 62 of the photo multiplier tube are made integral with each other and held by the transparent resin, and positioned by the transparent resin.

The transparent resin structure that integrates and holds the respective components is surrounded (enveloped) by the resin that uniformly contains a pigment, and the pigment has a wavelength characteristic to absorb the excitation light, the intrinsic fluorescence generated when the sample casing is irradiated with the excitation light, and the Raman light generated from the resin when the excitation light proceeds in the resin. Thus, the resin that contains the pigment constitutes the housing 63 (example of the "housing" in the claims) for holding the sample casing 57, the fluorescence measuring unit 59, the fluorescence collecting optical system and the like.

If necessary, at least part of the solid light source 55 and the fluorescence measuring unit 59 is buried in the pigment-containing resin, and a power source (not shown) for feeding electricity to the solid light source 55 and the fluorescence measuring unit 59 may also be buried in the pigment-containing resin.

Laser Light Source

The laser light source, which is used as the solid light source 55, is, for example, a diode-pumped solid-state (DPSS) laser device. Specifically, a green laser device that emits a laser beam at a wavelength of 532 nm, which is the second harmonic of the semiconductor-pumped (diode-pumped) Nd:YVO$_4$ laser (wavelength is 1064 nm), is used as the laser light source.

Sample (Measurement Target)

In this embodiment, the measurement sample is a kit that includes an antibody light chain variable region polypeptide and an antibody heavy chain variable region polypeptide. One of the antibody light chain variable region polypeptide and antibody heavy chain variable region polypeptide is labelled by the fluorescent dye. This kit is referred to as, for convenience, "antibody labelled by the fluorescent material."

The "antibody labelled by the fluorescent material" is a piece of a recombinant antibody, with the distal end (terminus) and its vicinity of the antibody being fluorescently labelled by the dye. The simple substance of this antibody is in a quenched state, i.e., the fluorescence of the dye is quenched by an amino acid in the antibody. When an antigen, which becomes a sample, is combined with the antibody labelled by the fluorescent material, the quenching is cancelled, and the fluorescence intensity of the dye significantly increases.

In other words, when the antibody labelled by the fluorescent material prior to the reaction with the antigen is irradiated with the laser beam, the fluorescence of the dye does not occur. However, when the "antibody labelled by the fluorescent material" that couples with the antigen is irradiated with the laser beam after the antibody labelled by the fluorescent material reacts with the antigen, an amount of the fluorescence from the dye increases.

When the above-described sample is used, the antigen is poured in the "antibody labelled by the fluorescent material" in the container and mixed with the "antibody labelled by the fluorescent material." Then, the resulting liquid mixture is irradiated with the laser beam (i.e., excitation light), and the generated fluorescence is measured. Such easy measurement can show the coupling state (coupling condition) between the antigen and the antibody. In other words, a solidifying step for solidify the antibody or the antigen in a microchip when the degree of the antibody-antigen reaction is measured with the microchip becomes unnecessary, and a cleaning step for removing nonspecific absorption of the labelling compound becomes unnecessary.

When the "antibody labelled by the fluorescent material" (i.e., measurement target) from which the quenching was cancelled due to the coupling with the antigen was irradiated with the laser beam having a wavelength of 532 nm, the fluorescence (example of "light emitted from the measurement target" in the claims) having a wavelength of 570-580 nm (example of "predetermined wavelength" in the claims) was emitted.

Sample Casing

For example, a polystyrene-made PCR tube is used as the sample casing 57. The PCR tube has a tapered end, and therefore bubbles are difficult to be generated at the end of the PCR tube even if a liquid sample is introduced. The PCR tube is positioned such that the end of the PCR tube is irradiated with the laser beam emitted from the DPSS laser device.

Optical System

On the optical path between the light emitting surface 61 of the DPSS laser device and the light receiving surface 62 of the photo multiplier tube, there are provided a first silicon resin 65 containing (enclosing) the light emitting surface 61 and the sample casing 57, a first air chamber 67 (example of "first lens" in the claims), a second silicon resin 69, a notch filter 71 (example of "second optical filter unit" in the claims), a third silicon resin 73, a second air chamber 75 (example of "second lens" in the claims), and the first optical filter 51 (structure 1). The components (i.e., first silicon resin 65, the first air chamber 67, the second silicon resin 69, the notch filter 71, the third silicon resin 73, the second air chamber 75, and the first optical filter) placed between the sample casing 57, from which the fluorescence emitted from the sample is emitted, and the light receiving surface 62 of the photo multiplier tube constitute the fluorescence collecting optical system.

The first to third silicon resins 65, 69 and 73 are transparent to the wavelength of the laser beam emitted from the DPSS laser device, to the wavelength of the fluorescence emitted from the sample and the like. The first to third silicon resins 65, 69 and 73 are made from, for example, PDMS (SIM-360 manufactured by Shin-Etsu Chemical Co., Ltd.).

The components of the optical system are surrounded (enclosed) by a pigment-containing resin that uniformly contains a pigment having a wavelength characteristic to absorb the excitation light, the intrinsic fluorescence generated when the sample casing is irradiated with the excitation light, and the Raman light generated from the resin when the excitation light proceeds in the resin (will be described later).

First Silicon Resin

The first silicon resin 65 includes the sample casing 57, and at least the light receiving surface of the DPSS laser. The first air chamber 67 is formed on the side opposite the sample casing 57 of the first silicon resin 65 (on the left side of the first silicon resin 65).

The first air chamber 67 is defined between the first silicon resin 65 and the second silicon resin 69. The interface between the first silicon resin 65 and the first air chamber 67 is shaped like a convex lens. Thus, the light emitting end of the first silicon resin 65 serves as the convex lens. By appropriately deciding a curvature, the convex lens (first silicon resin 65) shapes the diffusing light emitted from the sample to the parallel light.

Second Silicon Resin

In the second silicon resin 69, the prepared parallel light proceeds to the left in FIG. 6.

Notch Filter

A notch filter 71 is provided between the light emitting surface of the second silicon resin 69 and the light incident surface of the third silicon resin 73 such that the notch filter 71 firmly contacts the light emitting surface of the second silicon resin 69 and the light incident surface of the third silicon resin 73. In other words, the notch filter 71 is buried and held in the transparent PDMS resin of the second silicon resin 69 and the third silicon resin 73.

When the sample in the sample casing 57 placed in the first silicon resin 65 is irradiated with the laser beam (excitation light) of the DPSS laser device, not only the fluorescence is emitted from the sample but also the stray light is emitted from the first silicon resin 65 due to the excitation light having the 532 nm wavelength, together with the stray light (intrinsic fluorescence) emitted from the sample casing 57 and the Raman light generated when the stray light due to the excitation light proceeds in the PDMS resin. The wavelengths of the stray light and the Raman light are different from the wavelength of the fluorescence (570-580 nm) emitted from the sample (measurement target). Actual measurements indicated that all the wavelengths of the stray light and the Raman light were shorter than the wavelength of the fluorescence (570 nm).

The notch filter 71 has an incident angle characteristic. The notch filter 71 is selected to allow almost 100% of the fluorescence having the 570-580 nm wavelength (light from the measurement target) to pass therethrough when such fluorescence is incident at the 0-degree incident angle, and reflects almost 100% of the light having the 532 nm wavelength when such light is incident at the 0-degree incident angle. 532 nm is the wavelength of the excitation light. The light emitted from the second silicon resin 69 is parallel light, and the notch filter 71 is arranged such that the incident angle of the parallel light be zero degree. Thus, the stray light of the excitation light included in the parallel light emitted from the second silicon resin 69 is removed by the notch filter 71.

Although the stray light of the intrinsic fluorescence from the sample casing 57 and the Raman light generated when the stray light due to the excitation light proceeds in the PDMS resin pass through the notch filter 71, the intensity of the intrinsic fluorescence and the intensity of the Raman light are significantly smaller than the intensity of the stray light due to the excitation light, and substantially removed by the optical filter 51 of this embodiment (will be described later).

Third Silicon Resin

In the third silicon resin 73, the parallel light that has passed the notch filter 71 proceeds to the left in FIG. 6.

Optical Filter (Structure 1) of the Embodiment

An optical filter 51 that includes a dye diffusion restricting member 77 and a dye-containing silicon resin 79 was prepared to remove light other than the fluorescence emitted from the measurement target having the 570-580 nm wavelength (i.e., light from the measurement target), and the fluorescence to be measured and included in the stray light of the intrinsic fluorescence and the Rama light after the light passes through the third silicon resin 73.

The optical filter 51 was fabricated by a method that was based on the above-described first method of fabricating the structure 1. PMMA was used as the dye diffusion restricting member 77. A three-dimensional (3D) printer was used to fabricate the optical filter 51 in the form of a container having an opening at one end, as shown in FIG. 2A. This container was filled with the liquid PDMS, which is a mixture of the base resin or main agent (SIM-360) and the curing agent (CAT-360), and the liquid PDMS was solidified. Then, the container 24 filled with the PDMS was immersed in a dye solution, in which the Sudan I dye was dissolved in ethanol at the concentration of 18.0 mM, for 24 hours such that the Sudan I dye diffused in the PDMS resin. Thus, the optical filter 51 has the same characteristic as (or similar characteristic to) the optical filter which was prepared with the dye of the Example #(2) of FIGS. 4 and 5.

After the dye diffusion, those portions of the dye diffusion restricting member 77 which were in contact with the second air chamber 75 and the light receiving surface 62 of the photo multiplier tube, were removed, as shown in FIG. 6. Thus, the optical filter 51 has the dye diffusion restricting member 77 at only those portions of the optical filter 51 which contact the dye-containing resin (will be described).

The above-described second air chamber 75 was defined between the optical filter 51 and the third silicon resin 73. The interface between the light incident surface of the optical filter 51, at which the dye-containing silicon resin 79 is exposed, and the second air chamber 75 is shaped like a convex lens. The curvature of the convex lens shape is decided such that the parallel light incident to the optical filter 51 from the third silicon resin 73 ultimately collects (condenses) to the light receiving surface 62 of the photo multiplier tube.

As obvious from the characteristic of the dye of the Example #(2) shown in FIGS. 4 and 5, the optical filter 51 has a characteristic to absorb the light having the wavelength shorter than 570 nm. On the other hand, the wavelength of the stray light derived from the intrinsic fluorescence from the sample casing 57, which passes through the notch filter 71, and the wavelength of the stray light derived from the excitation light are shorter than 570 nm, as described above, and the intensity of the above-mentioned stray light is small. Thus, the stray light derived from the intrinsic fluorescence from the sample casing 57, and the stray light derived from the excitation light are almost completely removed by the optical filter 51 of this embodiment.

Pigment-Containing Silicon Resin

As described above, the optical path (space) through which the laser beam (i.e., excitation light) and the fluorescence emitted from the sample in the sample casing proceed, is defined by the transparent resin such as PDMS (first to third silicon resins 65, 69 and 73), the first and second air chambers 67 and 75, and the optical filter 51 of this embodiment. The optical path (space) is enclosed by the resin (housing 63) which uniformly contains a pigment. The pigment has a wavelength characteristic to absorb the excitation light, the intrinsic fluorescence generated when the sample casing is irradiated with the excitation light, and the Raman light emitted from the resin when the excitation light proceeds in the resin.

The silicon resin 63 that contains the pigment is the same silicon resin as the first to third silicon resin 65, 69 and 73 that forms the optical path, and the silicon resin 79 that constitutes the optical filter 51 and contains the dye. For example, the silicon resin 63 that contains the pigment is PDMS resin. A black pigment, which is made from carbon, is used as the pigment to be contained in the PDMS. The black pigment absorbs the stray light derived from the excitation light, the stray light derived from the intrinsic fluorescence, and the Raman light.

As described above, the pigment-containing silicon resin 63 is the same as the first to third silicon resin 65, 69 and 73 that define the optical path, and the dye-containing silicon resin that forms the optical filter 51 of this embodiment. Thus, these resin components have the same refractive index. In other words, there is no refractive index boundary between the pigment-containing silicon resin 63 and the first to third silicon resins 65, 69 and 73. Accordingly, when the stray light that passes through the region occupied by the first to third silicon resins 65, 69 and 73 is incident on the region occupied by the pigment-containing silicon resin 63, the light reflection and scattering are suppressed at the boundary (interface) between the pigment-containing silicon resin 63 and the first to third silicon resins 65, 69 and 73. The pigment-containing silicon resin 63 contacts the first to third silicon resins 65, 69 and 73 at the boundary.

Therefore, the respective stray light that proceeds in the optical path is incident on the pigment-containing silicon resin 63 without being reflected and scattered, and is absorbed by the pigment contained in the silicon resin 63.

On the other hand, a dye diffusion restricting member 77 is placed between the pigment-containing silicon resin 63 and the optical filter 51. The dye diffusion restricting member 77 is made from PMMA. There are refractive index boundaries at the interfaces between these components. It should be noted, however, that the stray light reflected and scattered at the refractive index boundaries are absorbed by the dye-containing silicon resin 79. In effect, therefore, the stray light does not arrive at the light receiving surface of the photo multiplier tube.

The light induced fluorescence measuring apparatus 53 shown in FIG. 6 has similar features (characteristics) to the measuring apparatus shown in FIG. 7. Specifically, the respective components are buried in the resin, and therefore the positional displacements of the optical elements and other parts are difficult to occur in the light induced fluorescence measuring apparatus 53 shown in FIG. 6. Thus, the measuring apparatus 53 is stable against the external shock. In addition, because holders to support the optical elements are not necessary, the light induced fluorescence measuring apparatus 53 can have a compact size and be portable.

Because the silicon resin 63 that encloses the optical path (space) substantially uniformly contains the pigment having a wavelength characteristic to absorb the excitation light, the intrinsic fluorescence generated when the sample casing is irradiated with the excitation light, and the Raman light emitted from the resin when the excitation light proceeds in the resin, the excitation light and the fluorescence, which is the light to be measured, are not emitted to the outside of the measuring apparatus 53. Also, the external light does not enter the fluorescence collecting optical system. Thus, highly precise measurement is possible. Once the excitation light and the stray light (e.g., reflection light of the excitation light, and the scattered light of the excitation light) are incident on the pigment-containing resin, the excitation light and the stray light are absorbed by the pigment-containing resin. Thus, complicated multiple reflection (multipath reflection) of the stray light hardly takes place. Therefore, the fluorescence collecting optical system does not have to cope with the complicated multiple reflection of the stray light and can be simplified. As a result, the downsizing of the light induced fluorescence measuring apparatus 53 can be achieved.

In the light induced fluorescence measuring apparatus 53, when the optical filter 51 is buried in the formed body 63 made from the silicon resin (e.g., PDMS), the dye diffusion restricting member 77 is provided at least in the region at which the structure 1 (optical filter 51) contacts the silicon resin 63 such that the interface between the optical filter 51 and the surrounding (enclosing) formed body made from the silicon resin 63 becomes the interface between the dye diffusion restricting member 77 and the silicon resin.

Therefore, the dye contained in the dye-containing silicon resin 79 of the optical filter 51 can hardly enter the dye diffusion restricting member 77 although the dye contained in the silicon resin 79 may move inside the silicon resin 79. Accordingly, the dye contained in the silicon resin 79 does not leak from the optical filter 51 into the formed body made from the silicon resin such as PDMS. In other words, the dye dispersed in the optical filter 51 does not move to the outside gradually, and the optical filter 51 can maintain the predetermined function.

It should be noted that an air layer may be provided instead of the diffusion restricting member 77. The air layer is able to suppress (prevent) the dye contained in the silicon resin 79 from leaking from the optical filter 51 into the formed body made from the silicon resin such as PDMS.

When the structure 1 contains a dye to absorb predetermined light and is used as the optical filter 51, the optical filter 51 serves as an organic light functional member that has a similar optical characteristic to the color glass filter. As described above, it is relatively easy to prepare the silicon resin by forming (molding), and the shape of the silicon resin has a high degree of freedom. Thus, it is possible to easily obtain an organic light functional member that has a shape corresponding to the shape of the optical path of the optical system.

Second Embodiment

Figure 8:
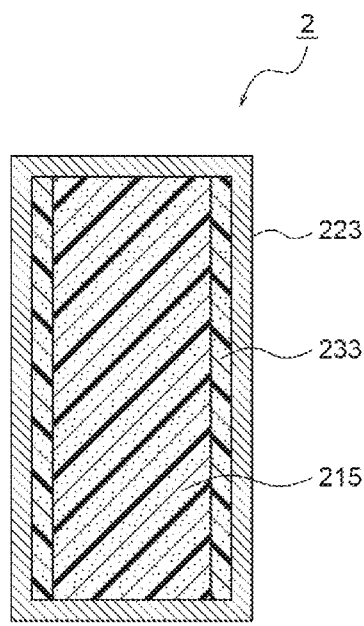
FIG. 8 illustrates a cross-sectional view of another structure according to another embodiment of the present invention.

Referring to FIG. 8, a structure 2 which is different from the structure 1 of the first embodiment will be described. FIG. 8 shows a cross-sectional view of the structure 2 according to the second embodiment. In the second embodiment, the structure 2 is configured as the optical filter 51, and the optical filter 51 is used in the light induced fluorescence measuring apparatus 53 (LIF measuring apparatus) shown in FIG. 6.

The structure 2 is different from the structure 1 in that the structure 2 includes a second dye-containing silicon resin 233 (example of "light absorbing unit" in the claims) between the dye diffusion restricting member 223 and the dye-containing silicon resin 215. The second dye (example of "second dye" in the claims) contained in the silicon resin 233 absorbs the fluorescence from the sample, the excitation light, the stray light derived from the intrinsic fluorescence and the Raman light. In this specification, the second dye includes a dye that does not dissolve in the water, and a pigment-like dye that does not move. Examples of the second dye include a carbon powder, a carbon nanotube and a black titanium oxide.

Figure 9A:
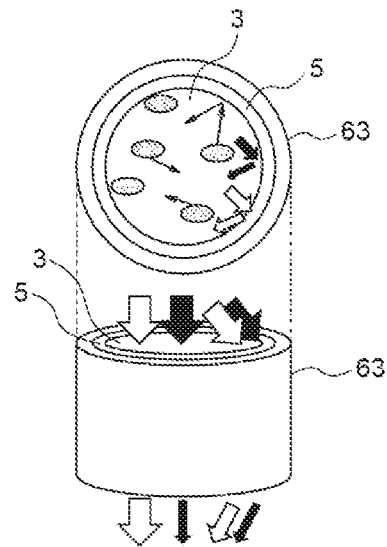
FIG. 9A is a pair of a cross-sectional view and a perspective view of the optical filter, showing quenching (extinction) of the excitation light and other light in the optical filter when the structure is used.
Figure 9B:
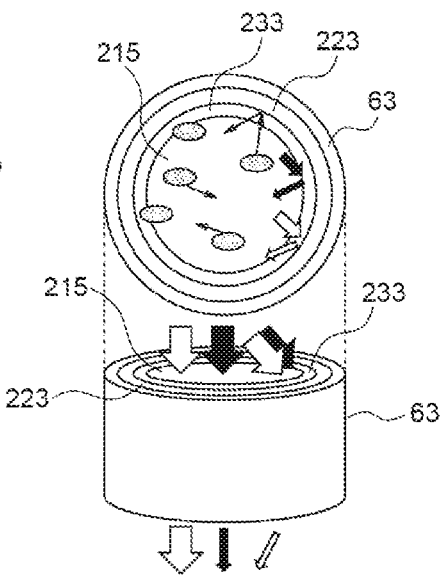
FIG. 9B is a pair of a cross-sectional view and a perspective view of the optical filter, showing quenching (extinction) of the excitation light and other light in the optical filter when said another structure is used; and FIGS. 10A to 10H

Extinction of the Excitation Light in the Optical Filter of the Second Embodiment Referring to FIGS. 9A and 9B, the advantages of the structure 2 will be described. Each of FIGS. 9A and 9B is a pair of a cross-sectional view and a lateral view of the optical filter 51 to show the extinction of the excitation light and other light in the optical filter 51. FIG. 9A uses the structure 1 as the optical filter 51, and FIG. 9B uses the structure 2 as the optical filter 51. In FIGS. 9A and 9B, the white arrows indicate the fluorescence emitted from the sample, and the black arrows indicate other light which is not the measurement target. In FIGS. 9A and 9B, the optical filter is enclosed (surrounded) by the housing 63 that has the pigment-containing resin.

Referring first to FIG. 9A, the extinction of the excitation light and other light is depicted when the structure 1 is used as the optical filter 51. Not only the fluorescence emitted from the sample but also the excitation light, the stray light of the intrinsic fluorescence from the sample casing 57 and the stray light derived from the excitation light are incident on the optical filter 51 from the third silicon resin 73 although the intensity of the excitation light, the stray light of the intrinsic fluorescence from the sample casing 57 and the stray light derived from the excitation light is small. When the above-mentioned light passes through the optical filter 51, the stray light of the intrinsic fluorescence and the stray light derived from the excitation light are almost absorbed by the dye-containing silicon resin 79, and only the fluorescence emitted from the sample is not absorbed. Therefore, it is possible to consider that the light that passes through the optical filter 51 and is incident on the measuring unit 59 is almost only the fluorescence emitted from the sample.

In reality, however, the stray light of the excitation light and the fluorescence may be incident on the interface between the two components having different refractive indices (between the dye diffusion restricting member 77 and the dye-containing silicon resin 79) in the structure 1. The scattered light of the excitation light and the fluorescence has a very small intensity as compared to the measurement target (fluorescence). Thus, it can be said that the scattered light of the excitation light and the fluorescence does not exert great influences on the measurement, but the scattered light of the excitation light and the fluorescence appears at the interface between the dye diffusion restricting member 77 and the dye-containing silicon resin 79.

FIG. 9B depicts the extinction of the excitation light and other light when the structure 2 is used as the optical filter 51. Similar to the structure 1, the stray light of the intrinsic fluorescence and the stray light derived from the excitation light are almost absorbed by the dye-containing silicon resin, and only the fluorescence emitted from the sample is not absorbed. There is a refractive index boundary between two components having different refractive indices (between the dye diffusion restricting member 223 and the second dye-containing silicon resin 233).

However, the structure 2 is different from the structure 1 in that the structure 2 includes the second dye-containing silicon resin 233 between the dye diffusion restricting member 223 and the dye-containing silicon resin 215, and the second dye contained in the silicon resin 233 absorbs the fluorescence from the sample, the excitation light, the stray light derived from the intrinsic fluorescence and the Raman light. Accordingly, the stray light of the fluorescence and the stray light of the excitation light which are incident on the interface between the dye diffusion restricting member 223 and the dye-containing silicon resin 215 are absorbed by the second dye-containing silicon resin 233, and it is possible to suppress the generation of the scattered light of the excitation light and the fluorescence. In addition, the second dye-containing silicon resin 233 is made from the same material (silicon resin) as the dye-containing silicon resin 215. Thus, neither the reflection light nor the scattered light is generated between the layer of the silicon resin 233 and the layer of the silicon resin 215. Consequently, when the structure 2 is used as the optical filter, it is possible to measure the fluorescence more precisely than when the structure 1 is used as the optical filter.

As shown in FIG. 9B, it is effective (advantageous) for the second dye-containing silicon resin 233 to have the layer thickness thinner than the size of the dye contained in the dye-containing silicon resin 215. When the layer thickness of the second dye-containing silicon resin 233 is thinner than the size of the dye contained in the dye-containing silicon resin 215, and the dye contained in the silicon resin 215 accidentally diffuses into the second dye-containing silicon resin 233, at least part of the dye remains in the dye-containing silicon resin 215. Accordingly, it is possible to easily suppress the deterioration of the function (performance) of the optical filter.

Method of Making the Structure 2

Figure 10A:
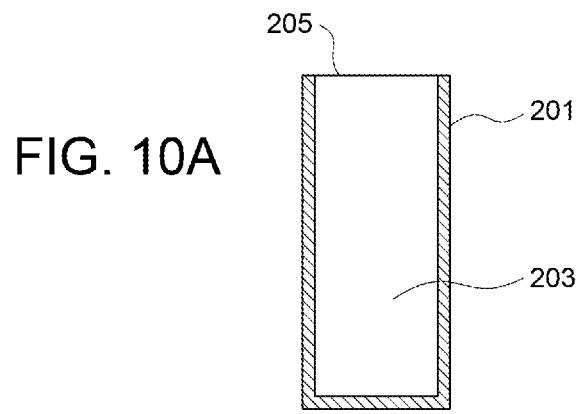
FIGS. 10J to 10M is a series of views useful to describe an exemplary method of fabricating said another structure that is made from a dye-containing silicon according to the present invention.

As shown in FIG. 10A, firstly a form member 201 is prepared. The form member 201 is made from, for example, an acrylic resin or a metal, and has a shape corresponding to the shape of the silicon resin such as PDMS that contains a dye in the optical filter. The optical filter is formed to a shape corresponding to the shape of the optical path in the measuring apparatus 53.

The form member 201 has a cavity (hollow portion) 203 therein, and also has an opening 205 that is spatially continuous to the cavity 203. A silicon resin such as PDMS that contains a dye is placed in the cavity 203 (will be described later).

Figure 10B:
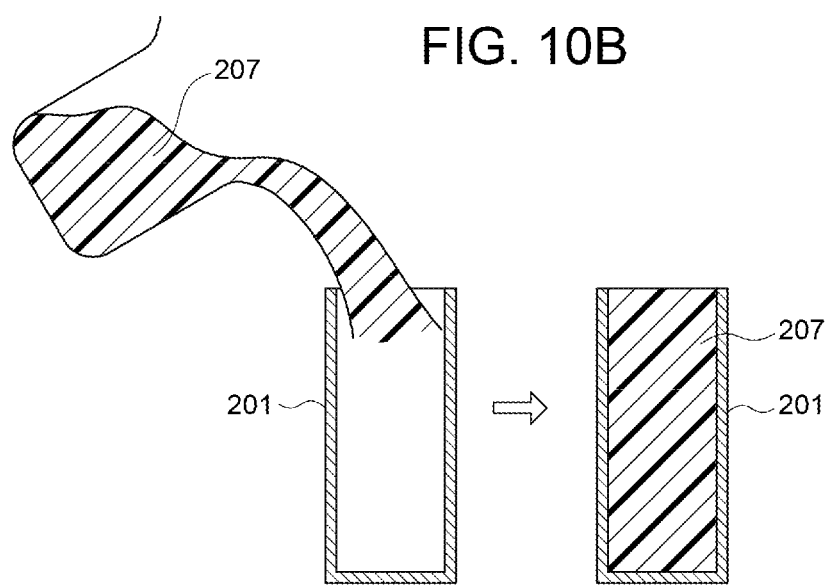

As illustrated in FIG. 10B, the liquid silicon resin 207 is poured from the opening 205 of the form member 201, and additives such as a polymerization initiator, a curing agent, a crosslinking agent and the like are appropriately added in accordance with the characteristic of the silicon resin used. Thus, the cavity 203 is filled with the liquid silicon 207 in which the additives are included.

Figure 10C:
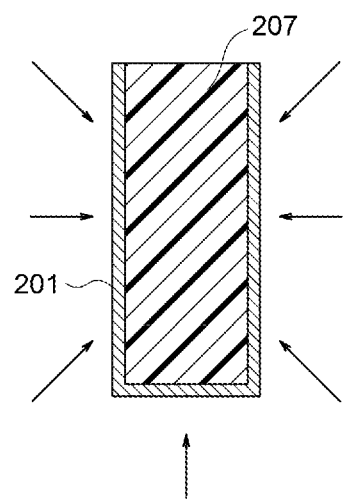

Subsequently, as shown in FIG. 10C, the liquid silicon resin 207 poured in the cavity 203 of the form member 201 is cured. The silicon resin 207 may be cured by leaving the form member 201 and the silicon resin 207 for a predetermined time at room temperature or by heating the form member 201 and the silicon resin 207 for a predetermined time, depending upon the type of the silicon resin. When the silicon resin 207 is the UV curable resin, the silicon resin 207 is irradiated with the curing beam for curing. FIG. 10C shows an example when the liquid silicon resin 207 is cured by heating. The black arrows in FIG. 10C represent the heating.

Figure 10D:
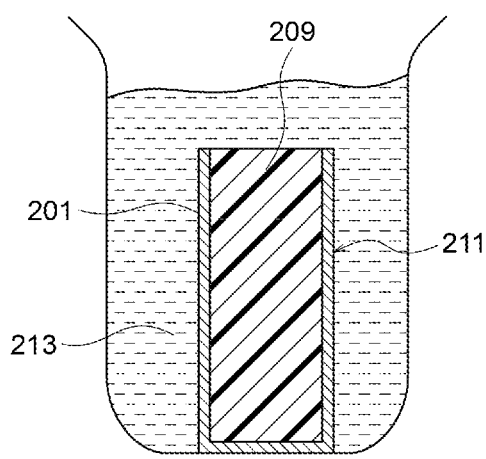

After that, a structure 211 is obtained. In the structure 211, the silicon resin 207 (209) is cured in the cavity 203, and becomes integral with the form member 201. The structure 211 is immersed in a dye solution 213, as shown in FIG. 10D. The dye solution 213 may be obtained by, for example, dissolving a dye in an organic solution such as alcohol.

Figure 10E:
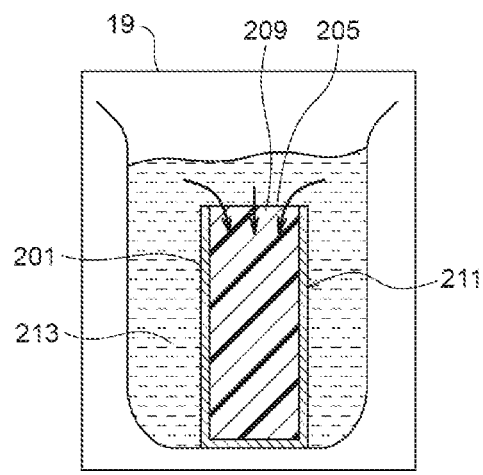

As shown in FIG. 10E, a thermostatic vessel or oven 19 (heating tank) or the like is used to heat the structure 211 immersed in the dye solution 213 for a predetermined time such that the dye diffuses in the silicon resin 209 from the opening 205.

Figure 10F:
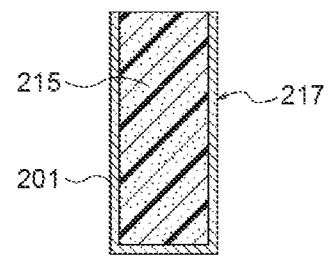

Then, as shown in FIG. 10F, the structure 217 having the dye-containing silicon resin 215 is taken out from the thermostatic vessel 19 or the like together with the dye solution 213, and the structure 217 is taken out from the dye solution 213. The structure 217 is left for a predetermined time at room temperature.

Figure 10G:
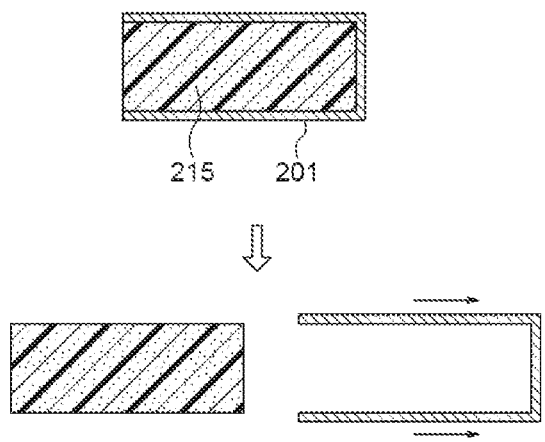

The above-described process is almost the same as the fabricating method of the structure 1. The method of fabricating the structure 2, however, includes an additional step of taking out the cured dye-containing silicon resin 215 from the form member 201 of the structure 217, as shown in FIG. 10G.

Figure 10H:
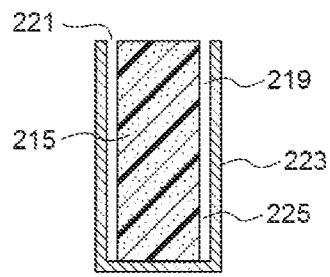

Subsequently, as shown in FIG. 10H, a dye diffusion restricting member 223 is prepared. The dye diffusion restricting member 223 is made from, for example, an inorganic glass and has a cavity 219 therein. The dye diffusion restricting member 223 has an opening 221 that is spatially continuous to the cavity 219. The cured dye-containing silicon resin 215, which is taken from the form member 201, is placed in the cavity 219. There is a gap 225 between the inner surface of the cavity 219 of the dye diffusion preventing member 223 and the outer surface of the cured dye-containing silicon member 215. The width of the gap 225 is the width of the second dye-containing silicon resin (will be described later). This width (or thickness) allows the second dye-containing silicon resin to sufficiently absorb the stray light of the excitation light and the like.

Figure 10J:
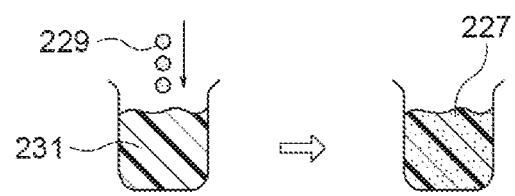

As shown in FIG. 10J, a liquid silicon resin 227 that contains a second dye 229 is prepared.

The second dye 229 is, for example, a black pigment which has a characteristic to absorb the stray light of the laser beam (i.e., the excitation light) and other light.

It should be noted that a coloring material (color) may be used as the second dye as long as the coloring material has a characteristic to absorb the above-mentioned stray light and other light. However, the coloring material is different from the pigment in that the coloring material moves in the silicon resin. Therefore, there is a possibility that the second dye leaks from the second dye-containing silicon resin into the dye-containing silicon resin, and the capability of the second dye-containing silicon resin to absorb the stray light and other light is deteriorated. Consequently, it is preferred to use, as the second dye, a pigment that does not move in the silicon resin.

As shown in FIG. 10J, the second dye 229 made from, for example, the black pigment is added to and mixed with the liquid silicon resin 231 to prepare the liquid silicon resin 227 that contains the second dye.

It should be noted that additives such as a polymerization initiator, a curing agent, a crosslinking agent and the like are appropriately added to the second dye-containing silicon resin 227 depending upon the characteristics of the silicon resin to be used.

Figure 10K:
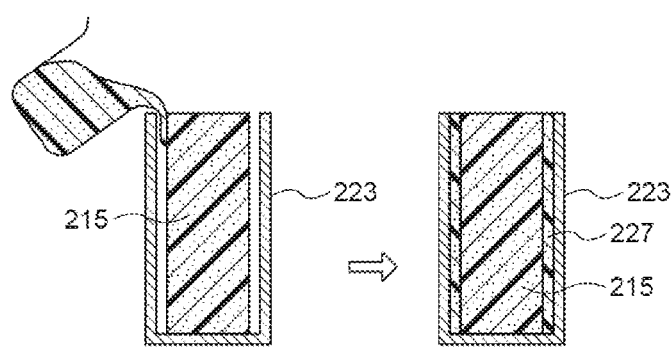

As shown in FIG. 10K, the liquid silicon resin 227 that contains the second dye (black pigment) is introduced to the gap 225 between the inner surface of the cavity 219 of the dye diffusion preventing member 223 and the outer surface of the cured dye-containing silicon resin 215, and the gap 225 is filled with the second dye-containing liquid silicon resin 227.

Figure 10L:
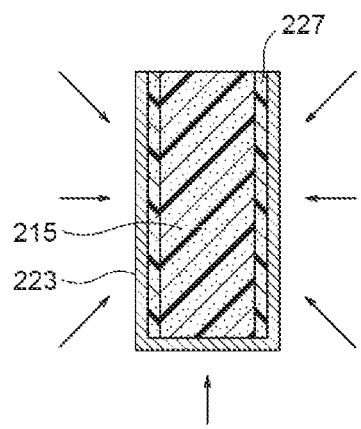

Subsequently, as shown in FIG. 10L, the liquid silicon resin 227 that contains the second dye (black pigment) poured into the gap 225 is cured. The silicon resin 227 may be cured by leaving the silicon resin 227 for a certain time at the room temperature, or by heating the silicon resin 227 for a certain time, depending upon the type of the silicon resin 227 to be used. When the silicon resin 227 is a UV curable resin, the silicon resin 227 is irradiated with a curing beam to cure the silicon resin 227. FIG. 10L shows an example when the liquid silicon resin 227 is cured by heating. The black arrows in FIG. 10L represent the heating.

The structure 2 is fabricated by the above-described process.

Figure 10M:
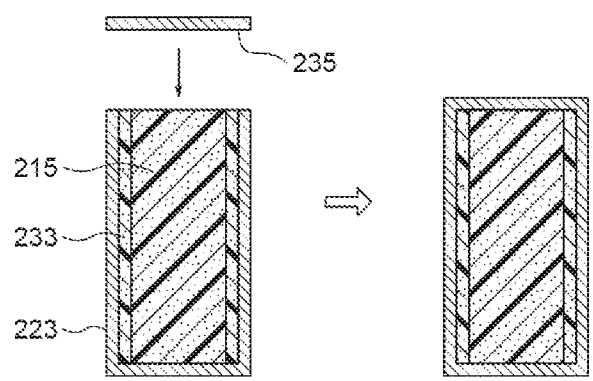

In the situation shown in FIG. 10L, the cured dye-containing silicon resin 215 and the second dye-containing silicon resin 233 are exposed at the opening 221 of the dye diffusion restricting member 223. If the exposed portions should also be covered with the dye diffusion restricting member 223, a lid member 235 that is made from the same (or similar) material as the dye diffusion restricting member 223 is attached over the opening 221, as shown in FIG. 10M. The lid member 235 is attached by, for example, welding.

When the cured dye-containing silicon resin 215 is prepared, a liquid silicon resin in which a dye is dispersed beforehand may be introduced in the form member 201 and the liquid silicon resin may be cured, as in the "Second Method of Making the Structure 1."

While certain embodiments have been described, these embodiments have been presented by way of example only, and are not intended to limit the scope of the present invention. The novel apparatuses and methods thereof described herein may be embodied in a variety of other forms; furthermore, various omissions, substitutions and changes in the form of the apparatuses and methods thereof described herein may be made without departing from the gist of the present invention. The accompanying claims and their equivalents are intended to cover such forms or modifications as would fall within the scope and gist of the present invention.

The present application is based upon and claims the benefit of a priority from Japanese Patent Application No. 2013-196082, filed Sep. 20, 2013 and a priority from Japanese Patent Application No. 2014-64415, filed Mar. 26, 2014, and the entire contents of which are incorporated herein by reference.

What is claimed is:

1. A filter member comprising:
a dye dispersed unit, in which a first dye is dispersed, and configured to allow, at least, light having a predetermined wavelength to pass therethrough, the first dye being operable to absorb that light which has a wavelength other than said predetermined wavelength; and
a dye diffusion restricting member provided adjacent to the dye diffused unit and configured to restrict diffusion of the first dye from the dye diffused unit.

2. The filter member according to claim 1 further comprising a light absorbing unit placed between the dye dispersed unit and the dye diffusion restricting member and configured to absorb light having a wavelength other than the predetermined wavelength.

3. The filter member according to claim 2, wherein the light absorbing unit is made from the same material as the dye dispersed unit, and contains a second dye which is different from the first dye.

4. The filter member according to claim 1, further comprising a second filter unit configured to absorb or reflect light having a wavelength other than the predetermined wavelength.

5. The filter member according to claim 1, wherein the dye diffused unit is made from silicone resin.

6. The filter member according to claim 1, wherein an entire surface of the dye diffused unit is covered with the dye diffusion restricting member.

* * * * *